United States Patent
Ho et al.

(10) Patent No.: US 10,161,844 B2
(45) Date of Patent: Dec. 25, 2018

(54) PARTICLE SENSING DEVICE AND ELECTRONIC APPARATUS HAVING THE SAME

(71) Applicant: Winbond Electronics Corp., Taichung (TW)

(72) Inventors: Yu-Hsuan Ho, Taichung (TW); Yi-Der Wu, Taichung (TW)

(73) Assignee: Winbond Electronics Corp., Taichung (TW)

( * ) Notice: Subject to any disclaimer, the term of this patent is extended or adjusted under 35 U.S.C. 154(b) by 0 days.

(21) Appl. No.: 15/252,245

(22) Filed: Aug. 31, 2016

(65) Prior Publication Data
US 2017/0292912 A1 Oct. 12, 2017

(30) Foreign Application Priority Data

Apr. 6, 2016 (TW) .............................. 105110757 A (51) Int. Cl.
*G01N 21/00* (2006.01)
*G01N 15/00* (2006.01)

(52) U.S. Cl.
CPC .................................. *G01N 15/00* (2013.01)

(58) Field of Classification Search
CPC ....... G01N 15/0205; G01N 2015/0046; G01N 21/59
USPC .......................................... 356/432, 336–338
See application file for complete search history.

(56) References Cited

U.S. PATENT DOCUMENTS 6,184,537 B1 * 2/2001 Knox ..................... G01N 21/53
250/574
6,285,291 B1 * 9/2001 Knox ..................... G08B 17/10
340/521
2009/0009748 A1 * 1/2009 Ahn ..................... G01N 15/065
356/37
2014/0356969 A1 12/2014 Nishikawa et al.
2016/0116389 A1 * 4/2016 Cooper ................. G08B 17/10
356/340

FOREIGN PATENT DOCUMENTS

TW 200730814 8/2007
TW 201506375 2/2015

OTHER PUBLICATIONS

"Office Action of Taiwan Counterpart Application," dated Apr. 19, 2017, p. 1-p. 5.

* cited by examiner

*Primary Examiner* — Isiaka Akanbi
(74) *Attorney, Agent, or Firm* — JCIPRNET (57) ABSTRACT

A particle sensing device, which senses a particulate matter by using a light beam from a light source, is provided. The particle sensing device includes a columnar array and a light-sensing element. The columnar array is disposed at a downstream side of a traveling path of the light beam. The columnar array has a plurality of columnar objects. A gap is existed between two adjacent columnar objects. The light-sensing element is disposed opposite to the columnar array and at a downstream side of a traveling path of the light beam. Wherein, the traveling path of the light beam is parallel with a length direction of each columnar object. And, the light beam passes through the gap for arriving at the light-sensing element. The particle sensing device can sense the particulate matter satisfactorily and can be simply integrated into various electronic apparatuses.

16 Claims, 7 Drawing Sheets

PARTICLE SENSING DEVICE AND ELECTRONIC APPARATUS HAVING THE SAME

CROSS-REFERENCE TO RELATED APPLICATION

This application claims the priority benefit of Taiwan application serial no. 105110757, filed on Apr. 6, 2016. The entirety of the above-mentioned patent application is hereby incorporated by reference herein and made a part of this specification.

BACKGROUND

Technical Field

The present disclosure relates to a particle sensing device, and in particular to a particle sensing device and an electronic apparatus having the same, which are able to detect the particulate matter (PM) in the air.

Description of Related Art

Particulate Matter 10 (PM 10) is referred to the fine particles with aerodynamic diameter less than or equal to 10 micrometer Such small particulate matters make them stay in the atmosphere for a long time and transport over long distance, and thus cause serious deterioration in air quality and visibility.

Figure 1:
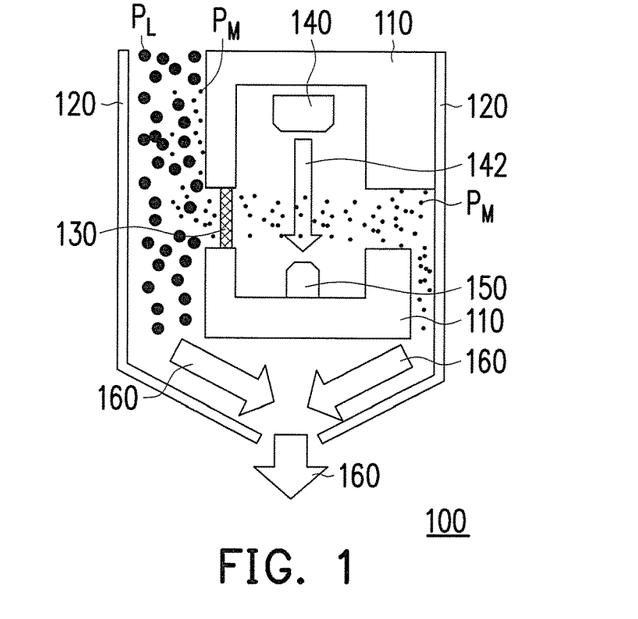
FIG. 1 is a schematic view of a conventional optical particle sensing device.

In addition, the particulate matters absorbing large amounts of toxic and hazardous substances can enter the human body via the body's respiratory system easily. PM 10 attaches to the body's respiratory system and organs easily. PM 2.5 is able to penetrate the alveoli directly and cycle whole body with the blood, which causes human diseases, such as allergies, asthma, emphysema, lung cancer, cardiovascular diseases, liver cancer, and blood diseases, etc. In order to detect the particulate matters in the atmosphere, there is a conventional optical particle sensing device as shown in FIG. 1. The optical particle sensing device 100 includes an inner housing 110, an outer housing 120, a filter screen 130, a light source 140 and a photodiode 150.

The outside air is drawn into the optical particle sensing device 100 through the air pump operation. As shown in FIG. 1, the air 160 flows in the space between the inner housing 110 and the outer housing 120 and transports the particulate matters with large diameter $P_L$ and the particulate matters with small diameter $P_M$. Then, the filter screen 130 filtrates the particulate matters with small diameter $P_M$ for detection, which makes said particulate matters enter the interior of the inner housing 110.

Figure 2:
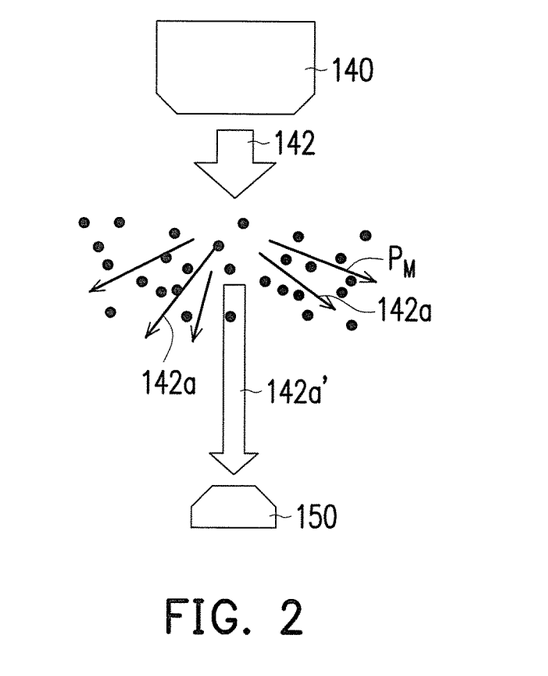
FIG. 2 is a partially enlarged view of a light source and a photodiode in FIG. 1.

FIG. 2 is a partially enlarged view of a light source and a photodiode in FIG. 1. Please referring to FIG. 1 and FIG. 2 simultaneously, the light source 140 and the photodiode 150 are disposed in the interior of the inner housing 110. The light source 140 and the photodiode 150 are disposed opposite to each other.

As shown in FIG. 2, the transmission path of the particulate matters with small diameter $P_M$ vertically passes through the traveling path of the light beam 142, and thus a lot of scattered light beams 142a are generated. The light intensity of the light beam 142a' finally reaching the photodiode 150 decreases because of the light scattering effect. Thus, the photocurrent of the photodiode 150 decreases accordingly, which achieves the function for detection of the particulate matters with small diameter $P_M$.

The necessity for detecting particulate matters in environment increases with great improvement. Due to the current particulate matter sensing devices still have the problems of inconvenient carrying, oversized dimensions and difficult integration, there is a strong demand to develop more convenient particulate matter sensing devices.

SUMMARY

The present disclosure provides a particle sensing device with low power consumption; such device can detect the particulate matters satisfactorily and can be integrated into various electronic apparatuses.

The present disclosure also provides an electronic apparatus, which can detect the particulate matters in environment easily.

The particle sensing device includes a columnar array and a light-sensing element. The columnar array is disposed at a downstream side of a traveling path of the light beam. The columnar array has a plurality of columnar objects. A gap is existed between two adjacent columnar objects. The light-sensing element is disposed opposite to the columnar array and at the downstream side of the traveling path of the light beam. The traveling path of the light beam is parallel with a length direction of each columnar object. And, the light beam passes through the gap for arriving at the light-sensing element.

The electronic apparatus according to the present disclosure, comprising: a device body and a particle sensing device. The device body has a light source, and the light source provides a light beam. The particle sensing device is electrically connected to the device body. The particle sensing device senses a particulate matter by utilizing the light beam from the light source. In one embodiment of the present disclosure, a material of the columnar objects includes a light-absorbing material.

In one embodiment of the present disclosure, the light-absorbing material is selected from a group consisting of black inorganic material, black organic material, black metal oxide and combinations thereof.

In one embodiment of the present disclosure, a size of the gap is from 4 μm to 12 μm.

In one embodiment of the present disclosure, the particle sensing device can further include a light filter, which is disposed at the downstream side of a traveling path of the light beam. The columnar array is disposed between the light filter and the light-sensing element.

In one embodiment of the present disclosure, the light filter filtrates a wavelength range from 400 nm to 500 nm of the light beam.

In one embodiment of the present disclosure, the light-sensing element includes a photodiode.

In one embodiment of the present disclosure, the light-sensing element includes a photovoltaic cell.

In one embodiment of the present disclosure, the particle sensing device is embedded in the device body of the electronic apparatus.

In one embodiment of the present disclosure, the electronic apparatus can further include an electrical connection element. The particle sensing device is connected to the device body of the electronic apparatus through the electrical connection element.

Based on above, the particle sensing device according to the embodiment of the present disclosure can utilize the columnar array for selecting the particulate matters with needed detection size and utilizing the columnar array for absorbing the scattered light beam, which increases the sensitivity of the light-sensing element.

In addition, the size of the particle sensing device can be very small, so that the particle sensing device can be integrated into various electronic apparatuses easily. Thus, the user can detect the particulate matters in environment to get the data of the density of the particulate matters at any time and utilize those data for subsequent related applications.

To make the above features and advantages of the present disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 3:
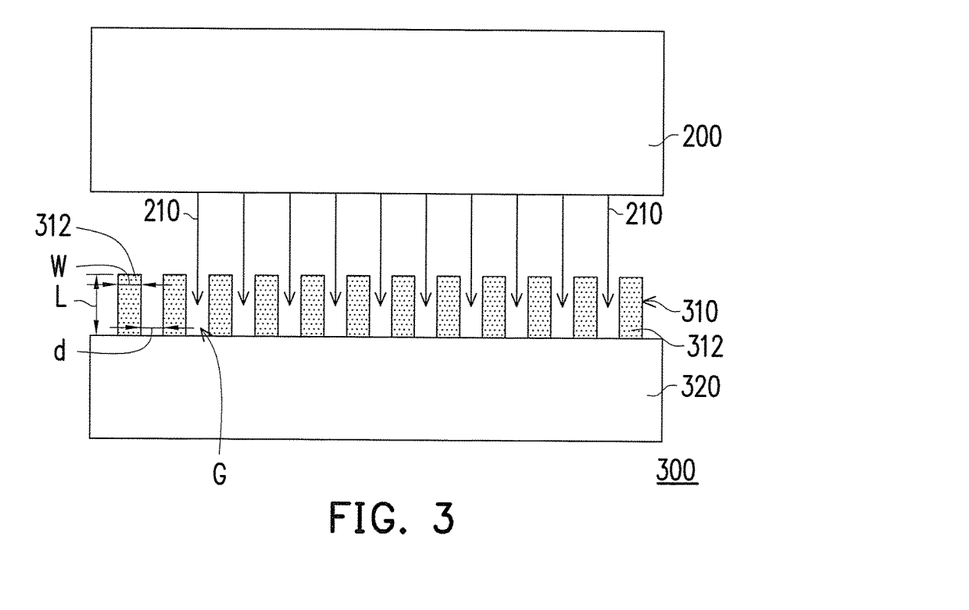
FIG. 3 is a schematic view of a particle sensing device according to one embodiment of the present disclosure.

FIG. 3 is a schematic view of a particle sensing device according to one embodiment of the present disclosure. Please referring to FIG. 3, the particle sensing device 300 detects particulate matters by utilizing the light beam 210 from the light source 200. The light source 200 as shown in FIG. 3 is for reference only, and the light source 200 can be any light sources, such as light-emitting diode backlight module, ambient light (sunlight, lights in environment) etc, which is not be limited.

Please referring to FIG. 3, the particle sensing device 300 can include a columnar array 310 and a light-sensing element 320. The columnar array 310 is disposed at a downstream side of a traveling path of a light beam 210. The columnar array 310 has a plurality of columnar objects 312. A gap G is existed between two adjacent columnar objects 312. The light-sensing element 320 is disposed opposite to the columnar array 310 and at a downstream side of the traveling path of the light beam 210. The traveling path of the light beam 210 is parallel with a length direction of each columnar object 312. And, the light beam 210 passes through the gap G for arriving at the light-sensing element 320.

Please referring to FIG. 3, in one embodiment of the present disclosure, the material of the columnar object 312 can be a light-absorbing material. The light-absorbing material can be selected from a group consisting of black inorganic material, black organic material, black metal oxide and combinations thereof. In detail, the light-absorbing material of the columnar object 312 can be selected based on the wavelength of the light beam 210, so as to suitably absorb the light beam 210.

And, each of the columnar object 312 can have the set width W and length L. The width W and length L of the columnar objects 312 and the size d of the gap G can be set, for example, in micro-meter order, to determine the particulate matters with a set size range for entering the gap G, so that the columnar array 310 can filter out the particulate matters with larger diameter in the air. In one embodiment of the present disclosure, the size of the gap G can be from 4 μm to 12 μm.

Please referring to FIG. 3, the light-sensing element 320 can be a photodiode or a photovoltaic cell. In one embodiment, the photovoltaic cell can be selected from inorganic photovoltaic cell or organic photovoltaic cell. The light-sensing element 320 can convert the light signals into electrical signals. The light-sensing element 320 can detect the change of light intensity (photocurrent) of the light beam 210 passed though the columnar array 310, so as to determine the density of the particulate matters in the space.

Figure 4:
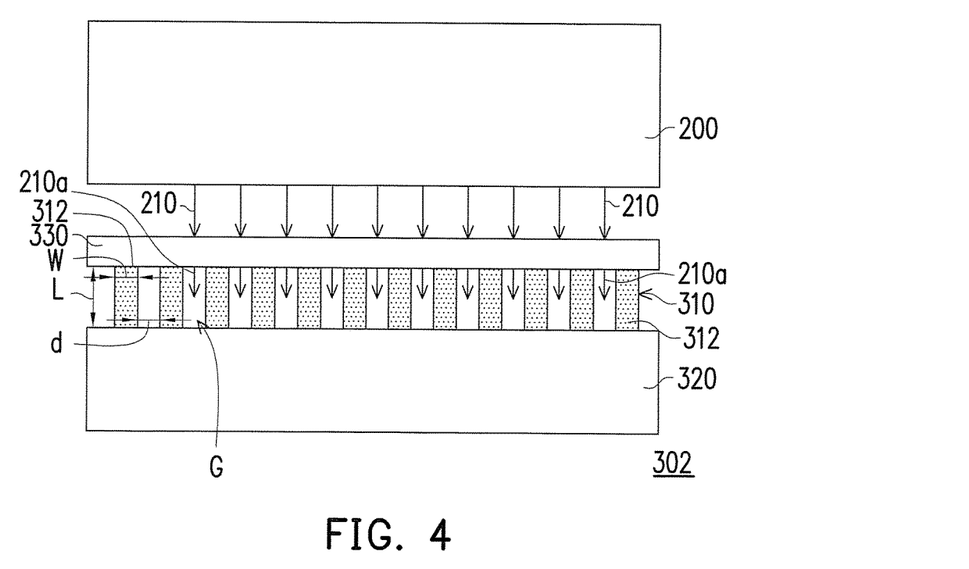
FIG. 4 is a schematic view of a particle sensing device according to another embodiment of the present disclosure.

FIG. 4 is a schematic view of a particle sensing device according to another embodiment of the present disclosure. In FIG. 4 and FIG. 3, identical elements are represented by the same reference numbers, and detailed descriptions thereof are not repeated hereinafter. Please referring to FIG. 4, in this embodiment, the particle sensing device 302 can further include a light filter 330, which is disposed at a downstream side of a traveling path of the light beam 210. The columnar array 310 is disposed between the light filter 330 and the light-sensing element 320.

Please referring to FIG. 4, the light filter 330 a wavelength range from 400 nm to 500 nm of the light beam 210. In other words, the light beam 210 becomes the light beam 210a (the wavelength can be range from 400 nm to 500 nm) after passing the light filter 330 and is incident into the gap G and then reaches to the light-sensing element 320. The function of the light filter 330 is to select the suitable wavelength corresponding to the absorption spectrum of the light-sensing element 320 and to purify the light source 200 for reducing the background noise simultaneously.

Figure 5:
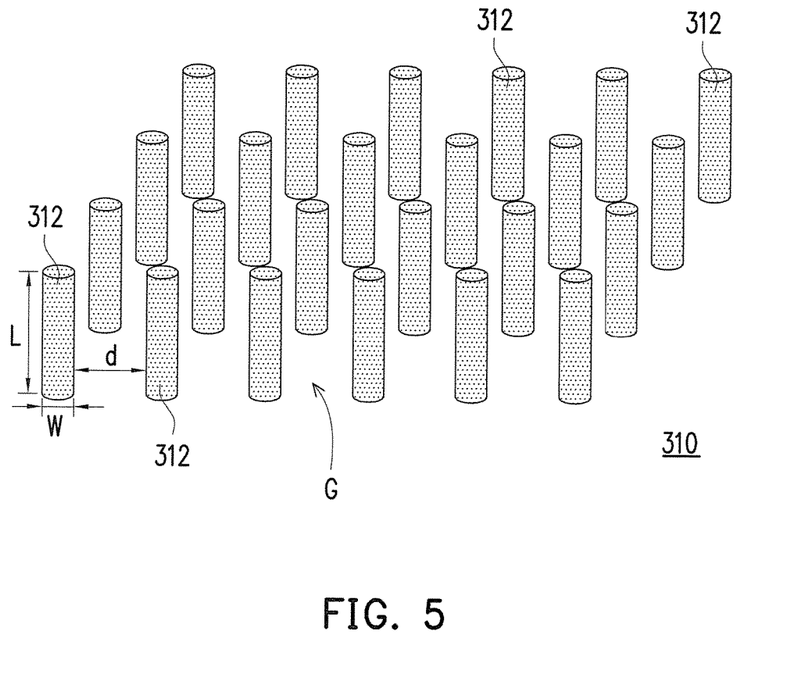
FIG. 5 is a partially three-dimensional schematic view of the columnar array according to one embodiment of the present disclosure.

FIG. 5 is a partially three-dimensional schematic view of the columnar array according to one embodiment of the present disclosure. Please referring to FIG. 4 and FIG. 5 simultaneously, the columnar array 310 can be supported between the light-sensing element 330 and light filter 320. Due to the columnar objects 312 are consisted of the strong light-absorbing material, when the particulate matters enter the gap G and scatter the light beam 210a, the columnar objects 312 can fully absorb the scattered light and avoid the secondary reflection of the scattered light. As a result, the interference of detection of the light-sensing element 320 caused by the scattered light is reduced, and the sensitivity of the light-sensing element 320 is increased.

In addition, the columnar array 310 can have regular gap G (having set size d), so that the columnar array 310 can select the suitable diameter of the particulate matters for detection. It also means that, the sizes of the columnar objects 312 (the length L and width W) and the size d of the gap G can be set to select PM 2.5 and PM 10, which are harmful to human body, for detection.

Hereinafter, accompanying with the related content according to FIG. 6~FIG. 10, takes the particle sensing device 302 according to FIG. 4 for an example to explain the detection principle and the mechanism of the particle sensing device 302 in the embodiment of the present disclosure.

Figure 6:
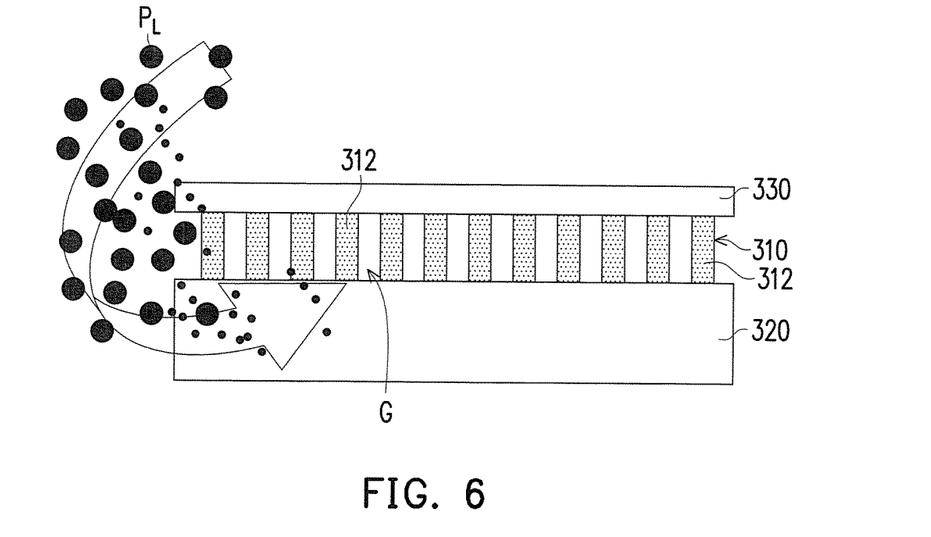
FIG. 6 is a schematic view of using the particle sensing device in FIG. 4 for detection, which shows the state of the particulate matters blocked by the columnar array.
Figure 7:
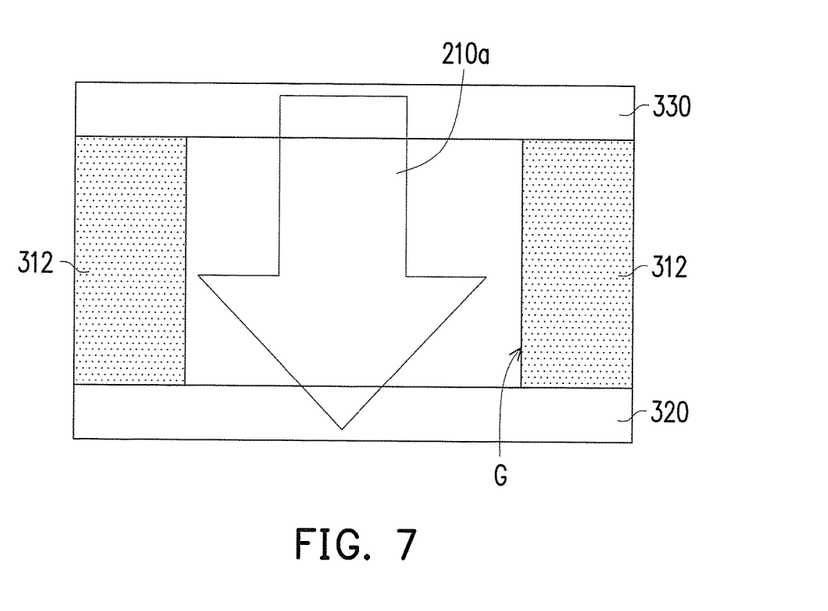
FIG. 7 is a partially enlarged schematic view of the particle sensing device in FIG. 6.

FIG. 6 is a schematic view of using the particle sensing device in FIG. 4 for detection, which shows the state of the particulate matters blocked by the columnar array. FIG. 7 is a partially enlarged schematic view of the particle sensing device in FIG. 6. Please referring to FIG. 6 and FIG. 7 simultaneously, the particulate matters with large diameter $P_L$ from the outside environment are blocked by the columnar array 310 and can not enter the gap G. When the gap G of the columnar array 310 isn't filled with the particulate matters having large diameter $P_L$, the light beam 210a can fully reach to the light-sensing element 320 and be absorbed by the light-sensing element 320 to generate high current.

Figure 8:
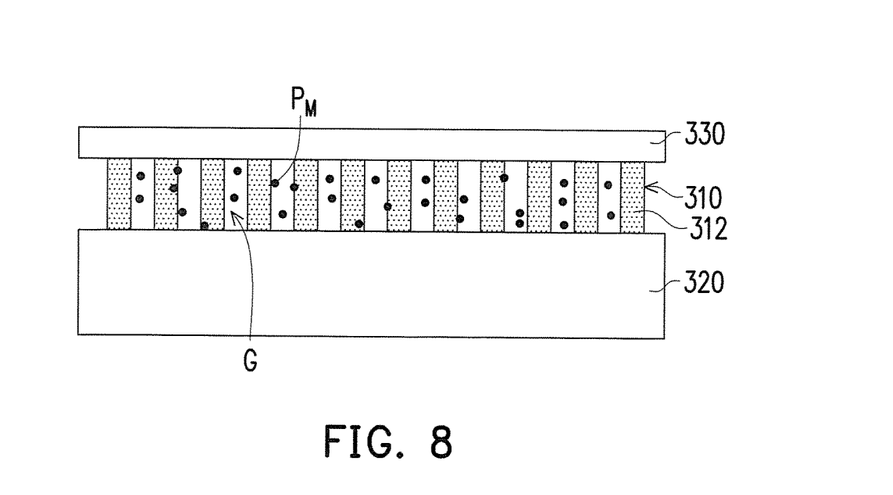
FIG. 8 is a schematic view of using the particle sensing device in FIG. 4 for detection, which shows the state of the particulate matters entering the gap of the columnar array.
Figure 9:
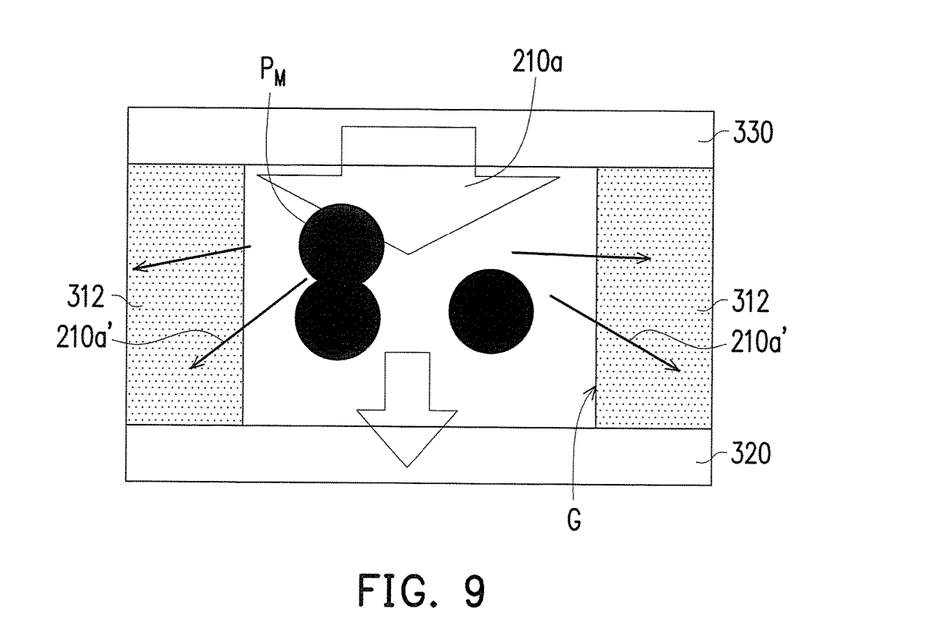
FIG. 9 is a partially enlarged schematic view of the particle sensing device in FIG. 8.

FIG. 8 is a schematic view of using the particle sensing device in FIG. 4 for detection, which shows the state of the particulate matters entering the gap of the columnar array. FIG. 9 is a partially enlarged schematic view of the particle sensing device in FIG. 8.

Please referring to FIG. 8 and FIG. 9 simultaneously, the particulate matters with small diameter $P_M$ from the outside environment can enter the gap G of the columnar array 310. The particulate matters with small diameter $P_M$ can scatter the light beam 210a, which generates a lot of the scattered light beam 210a'. And, the scattered light beam 210a' is incident toward the columnar objects 312. Due to the columnar object 312 is consisted of light-absorbing material, secondary reflection of the scattered light beam 312a' will not be generated, and the detection of the light-sensing element 320 will not be interfered. As this moment, the under light-sensing element 320 detects the decreased photocurrent caused by the decreased incident light intensity. Thus, the photocurrent value relating to the particulate matters with small diameter $P_M$ is obtained.

In detail, the loss of the incident light intensity caused by the scattering from the particulate matters with small diameter $P_M$ is proportional to the density of the particulate matters with small diameter $P_M$. Thus, the density of the particulate matters with small diameter $P_M$ can be detected by means of measuring the loss value of the incident light intensity and multiplying such value by a conversion calibration coefficient (the unit is "density/ampere"). The detailed description is given as follows.

Figure 10:
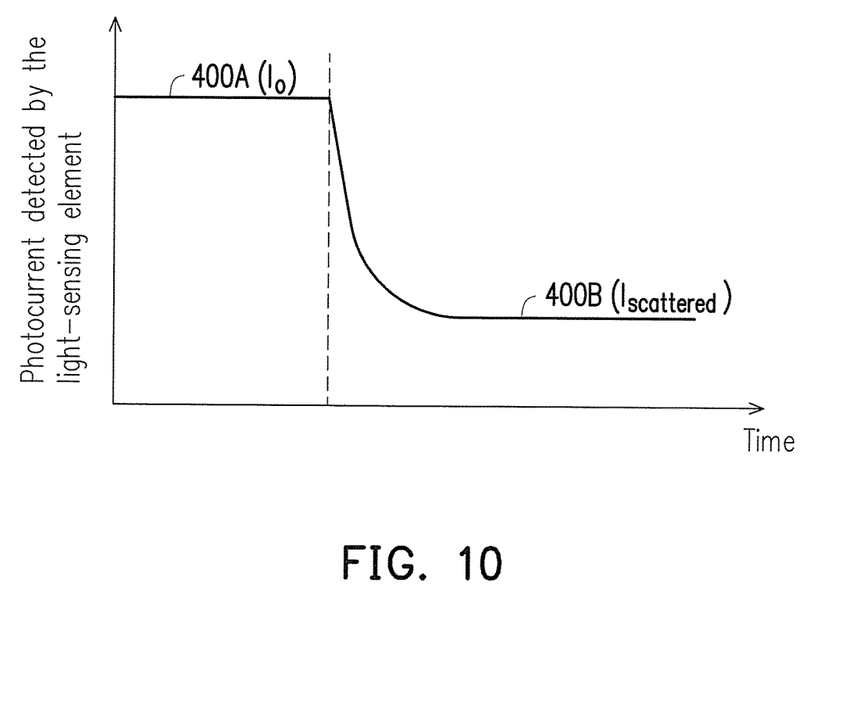
FIG. 10 is a schematic view of the curve of change in photocurrent detected by the light-sensing element of the particle sensing device according to one embodiment of the present disclosure.

FIG. 10 is a schematic view of the curve of change in photocurrent detected by the light-sensing element of the particle sensing device according to one embodiment of the present disclosure. As shown in FIG. 10, the vertical axis refers to the photocurrent detected by the light-sensing element, and the horizontal axis refers to the time. The curve 400A stands for the state of the particle sensing device inhaling clean air and the curve 400B stands for the state the particle sensing device inhaling the particulate matters.

Please referring to FIG. 10, in the state of curve 400A (inhaling clean air), the measured photocurrent is $I_0$. In the state of curve 400B (inhaling the particulate matters), the measured photocurrent is $I_{scattered}$. Due to the loss value of the photocurrent is proportional to the density of the particulate matters, the density of the particulate matters can be calculated by the following formula (1).

$$D_{particle} = c \times (I_0 - I_{scattered}) \quad (1)$$

wherein, $D_{particle}$ is the density of the particulate matters.
c is the calibration constant (density/ampere).
$I_0$ is the measured photocurrent (ampere) in the state in clean air.
$I_{scattered}$ is the measured photocurrent (ampere) in the state during inhaling the particulate matters.

Figure 11:
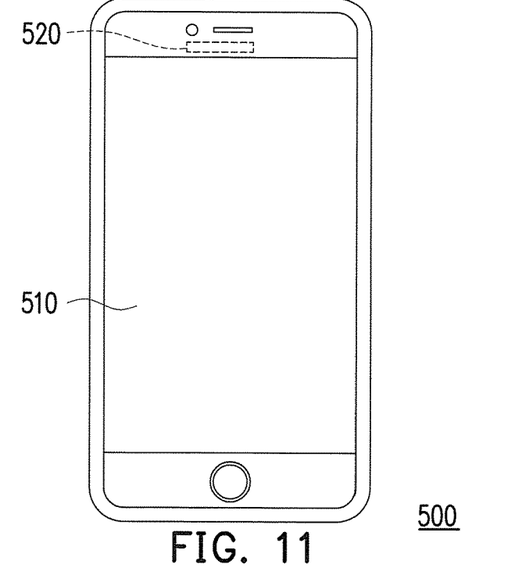
FIG. 11 is a schematic view of the electronic apparatus according to one embodiment of the present disclosure.

FIG. 11 is a schematic view of the electronic apparatus according to one embodiment of the present disclosure. Please referring to FIG. 11, the electronic apparatus 500 can includes a device body 510 and a particle sensing device 520. And, the particle sensing device 520 can be the particle sensing device 300 in FIG. 3 or the particle sensing device 302 in FIG. 4. Detailed descriptions about the particle sensing device 520 are not repeated hereinafter.

Please referring to FIG. 3 and FIG. 11 simultaneously, the device body 510 has the light source 200 and the light source provides the light beam 210. The particle sensing device 520 is electrically connected to the device body 510. Notice that, in the embodiment as shown in FIG. 11, the particle sensing device 520 is embedded in the device body 510 of the electronic apparatus 500.

The electronic apparatus 500 can be any portable electronic device, such as smartphone, tablet computer, laptop computer, virtual reality display, wearable electronic device (such as smartbracelet, smartglasses), etc. In detail, the particle sensing device 520 according to the embodiment of the present disclosure can be integrated into any electronic apparatus, so that people can detect the particulate matters in environment to get the data of the density of the particulate matters at any time and utilize those data for subsequent related applications.

For example, in the application about the wearable electronic device, when the user wears the smartbracelet and does activities in any environment, the particle sensing device 520 integrated into the smartbracelet can utilize the ambient light to detect the density of the particulate matters in the environment in real time, and can report the detection result to the user. When the user realizes the excessive density of the particulate matters in the environment, he or she can take responses immediately, such as leaving the environment or wearing protective mask, etc.

For another example, in the application about the virtual reality display, when the user wears the virtual reality display and is in an environment, the particle sensing device 520 integrated into the virtual reality display can detect the density of the particulate matters in the environment, and can convert the density data into the visible image. The user can see the virtual appearance of the particulate matters in the environment (For example, the user sees intensive particulate matters when the density of particulate matters is high; or the user sees fresh natural environment when the density of particulate matters is low).

Please referring to FIG. 3 and FIG. 11, the columnar array 310 and the light-sensing element 320 are disposed "at a downstream side of a traveling path of the light beam 210", which means that in the electronic apparatus 500, the particle sensing device 520 can be disposed directly below the light source 200 of the electronic apparatus 500. In addition, a partial light beam of the backlight module of the electronic apparatus 500 can also be transmitted to the particle sensing device 520 by suitable light-guiding design, so as to detect the particulate matters. In other words, the degree of design freedom of the particle sensing device 520 can be increased.

Figure 12:
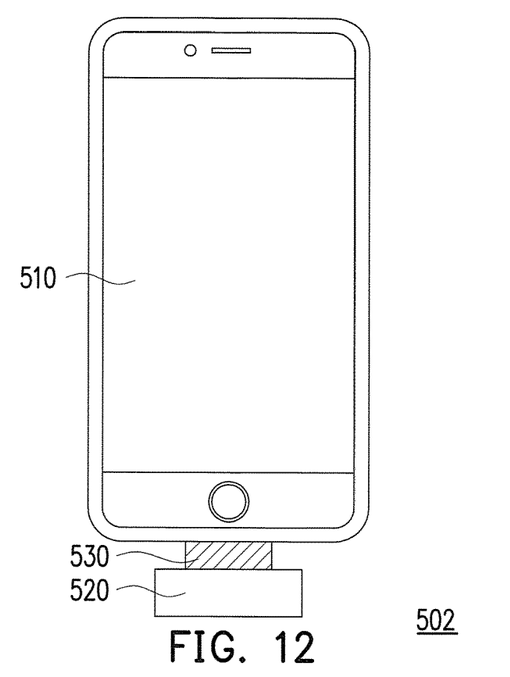
FIG. 12 is a schematic view of the electronic apparatus according to another embodiment of the present disclosure.

FIG. 12 is a schematic view of the electronic apparatus according to another embodiment of the present disclosure.

Please referring to FIG. 12, the electronic apparatus 502 can further includes an electrical connection element 530. The particle sensing device 520 is connected to the device body 510 of the electronic apparatus 502 through the electrical connection element 530. The connection ways of the electrical connection element 530 can be Universal Serial Bus (USB) or other suitable electrical connection ways, which is not limited.

The electronic apparatus 502 as shown in FIG. 12 can use the particle sensing device 520 by utilizing the external connection ways. The particle sensing device 520 can be disassembled when it is not needed to be used. By the above external connection ways, the flexibility and the degree of freedom of using the particle sensing device 520 and the electronic apparatus 502 is improved significantly.

And, the electronic apparatus 500 and 502, as shown in FIG. 11 and FIG. 12, can generate wireless signals to transmit the information about the photocurrent to the device body 510 by utilizing induction coil solenoid or Radio Frequency Identification (RFID), when the light-sensing element 320 of the particle sensing device 520 detects the light beam and generates the photocurrent.

The particle sensing device 300, 302 and 520 according to the embodiment of the present disclosure can utilize the ambient light or the light source of the electronic apparatus, and almost only the light-sensing element 320 needs power supply. Thus, the particle sensing device 300, 302 and 520 has very low power consumption. And, the particle sensing device 300, 302 and 520 can be integrated into any portable electronic device easily. The user can detect the density of particulate matters in the air in anytime and anywhere by the portable electronic device (such as smartphone). The detected data can also be applied in the related technical field of Internet of Things (IoT), and Big data. The interpretation of these data can create huge contribution in the field of atmospheric science, environment science, epidemiology, environmental protection and medicine, etc.

In summary, the particle sensing device and the electronic apparatus of the present disclosure at least have the following technical effects. The sensitivity of the light-sensing element can be improved by utilizing the columnar array to select the particulate matters with needed detection size and utilizing the columnar array to absorb the scattered light beam. And, the power consumption of the particle sensing device is very low. Moreover, the light filter can be used to select the wavelength range of the incident light beam, which increases the sensitivity of the light-sensing element. The size of the particle sensing device can be very small, so that the particle sensing device can be integrated to various electronic apparatuses easily.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A particle sensing device, which senses a particulate matter by using a light beam from a light source, and the particle sensing device comprising:
   a columnar array, being disposed at a downstream side of a traveling path of the light beam, wherein the columnar array has a plurality of columnar objects arranged in an array on a plane, each of the columnar object is a solid column spaced away from one another, made of a material comprising a light-absorbing material, and the light beam travels in a gap existed between every two adjacent columnar objects; and
   a light-sensing element, being disposed at a side of the columnar array and at the downstream side of the traveling path of the light beam;
   wherein the traveling path of the light beam is parallel with a length direction of each columnar object, and the light beam passes through the gap prior to arriving at the light-sensing element.

2. The particle sensing device as claimed in claim 1, wherein
   the light-absorbing material is selected from a group consisting of black inorganic material, black organic material, black metal oxide and combinations thereof.

3. The particle sensing device as claimed in claim 1, wherein
   a size of the gap is from 4 μm to 12 μm.

4. The particle sensing device as claimed in claim 1, further comprising:
   a light filter, being disposed at the downstream side of the traveling path of the light beam,
   wherein the columnar array is disposed between the light filter and the light-sensing element.

5. The particle sensing device as claimed in claim 4, wherein
   the light filter filtrates a wavelength range from 400 nm to 500 nm of the light beam.

6. The particle sensing device as claimed in claim 1, wherein
   the light-sensing element comprises a photodiode.

7. The particle sensing device as claimed in claim 1, wherein
   the light-sensing element comprises a photovoltaic cell.

8. An electronic apparatus, comprising:
   a device body, having a light source and the light source provides a light beam; and
   a particle sensing device, being electrically connected to the device body, and the particle sensing device senses a particulate matter by using the light beam from the light source, and the particle sensing device comprising:
   a columnar array, being disposed at a downstream side of a traveling path of the light beam, wherein the columnar array has a plurality of columnar objects arranged in an array on a plane, each of the columnar object is a solid column spaced away from one another, made of a material comprising a light-absorbing material, and the light beam travels in a gap existed between every two adjacent columnar objects; and
   a light-sensing element, being disposed at a side of the columnar array and at the downstream side of the traveling path of the light beam;
   wherein the traveling path of the light beam is parallel with a length direction of each columnar object, and the light beam passes through the gap prior to arriving at the light-sensing element.

9. The electronic apparatus as claimed in claim 8, wherein
   the light-absorbing material is selected from a group consisting of black inorganic material, black organic material, black metal oxide and combinations thereof.

10. The electronic apparatus as claimed in claim 8, wherein
    a size of the gap is from 4 μm to 12 μm.

11. The electronic apparatus as claimed in claim 8, wherein
    the particle sensing device further comprising:
    a light filter, being disposed at the downstream side of the traveling path of the light beam,
    wherein the columnar array is disposed between the light filter and the light-sensing element.

12. The electronic apparatus as claimed in claim 11, wherein
   the light filter filtrates a wavelength range from 400 nm to 500 nm of the light beam.

13. The electronic apparatus as claimed in claim 8, wherein
   the light-sensing element comprises a photodiode.

14. The electronic apparatus as claimed in claim 8, wherein
   the light-sensing element comprises a photovoltaic cell.

15. The electronic apparatus as claimed in claim 8, wherein
   the particle sensing device is embedded in the device body of the electronic apparatus.

16. The electronic apparatus as claimed in claim 8, further comprising:
   an electrical connection element, and
   the particle sensing device is connected to the device body of the electronic apparatus through the electrical connection element.

* * * * *